United States Patent [19]

Desbois

[11] Patent Number: 4,618,726

[45] Date of Patent: Oct. 21, 1986

[54] PROCESS FOR THE PREPARATION OF BENZOPHENONES

[75] Inventor: Michel Desbois, Rillieux, France

[73] Assignee: Rhone-Poulenc Specialites Chimiques, France

[21] Appl. No.: 683,171

[22] Filed: Dec. 18, 1984

[30] Foreign Application Priority Data

Dec. 22, 1983 [FR] France .................. 83 20537

[51] Int. Cl.$^4$ ............................................ C07C 45/47
[52] U.S. Cl. .................................. 568/322; 568/323; 568/42; 568/43
[58] Field of Search ................... 568/42, 43, 323, 322

[56] References Cited

U.S. PATENT DOCUMENTS

| | | | |
|---|---|---|---|
| 2,580,300 | 12/1951 | Johnson et al. | 568/323 |
| 3,956,240 | 5/1976 | Dahl et al. | 568/322 |
| 4,453,012 | 6/1984 | Desbois | 568/323 |
| 4,454,350 | 6/1984 | Desbois | 568/323 |

OTHER PUBLICATIONS

Olah "Friedel-Crafts & Related Reactions," Interscience Publn., vol. 1, p. 120, vol. III, pp. 1257–1258 (1963).
Hansch et al., Journal of Medicinal Chemistry, 16, No. 11, 1207–1212 and 1216, (1973).
Sheppard, Journal of Organic Chemistry, 29, No. 1, 1–11 (1964).

Primary Examiner—James H. Reamer
Attorney, Agent, or Firm—Finnegan, Henderson, Farabow, Garrett & Dunner

[57] ABSTRACT

A process for the preparation of benzophenones. A compound of the formula $COX_4X_5$, where $X_4$ and $X_5$, which may be identical or different are halogen atoms, is reacted, in liquid hydrofluoric acid, with a deactivated benzene derivative, in the presence of boron trifluoride in such amount that the absolute pressure of boron trifluoride in the reaction space is at least one bar.

15 Claims, No Drawings

PROCESS FOR THE PREPARATION OF BENZOPHENONES

The present invention relates to a process for the preparation of benzophenones.

Documents describing the preparation of these compounds may be found in the prior art.

In particular there may be mentioned "OLAH, FRIEDELCRAFTS AND RELATED REACTIONS"—III—Part I—1964 Interscience Publishers, page 8 et seq., which describes the preparation of 4,4'-difluorobenzophenone from 4-fluorobenzoyl chloride and fluorobenzene in the presence of aluminum trichloride. The disadvantages of this type of process are to be found especially in the fact that 4-fluorobenzoyl chloride is a compound which is difficult to obtain. In fact, five stages, starting from toluene, are necessary to produce it and its cost is evidently greatly affected thereby. A further disadvantage is the large amount of catalyst which it is necessary to employ (about 1 mole of catalyst per mole of substrate). Moreover, this catalyst cannot be recycled and it is necessary to provide very expensive treatments to destroy it so as to avoid any pollution.

There may also be mentioned HOUBEN-WEYL, Volume VII, 2a, page 234, which describes the preparation of 4,4'-difluorobenzophenone from fluorobenzene and phosgene in the presence of aluminum chloride as a catalyst. In this case, again, the same disadvantages due to the presence of aluminum chloride catalyst are encountered as those enumerated above.

We have now found a process of preparation which makes it possible to dispense with the presence of a catalyst such as $AlCl_3$.

Accordingly the present invention relates to a process for the preparation of benzophenones, which comprises reacting a deactivated benzene derivative with a compound of the general formula:

$$COX_4X_5 \qquad (I)$$

where $X_4$ and $X_5$, which may be identical or different, represent a halogen atom, in liquid hydrofluoric acid and in the presence of boron trifluoride in such an amount that the absolute pressure of boron trifluoride in the reaction space is at least 1 bar.

For the purposes of the present invention, a deactivated benzene derivative is a compound of the general formula (II):

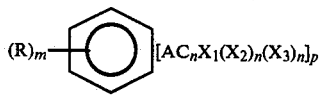

(II)

where
A is a covalent bond or an oxygen or sulfur atom,
$X_1$, $X_2$ and $X_3$ are identical or different and each is a halogen atom, n is between 0 and 2 and if A is a covalent bond, n is 0. p is 1 or 2,
R is chosen from among hydrogen and halogen. hydroxyl, alkyl, preferably $C_1$–$C_6$ alkyl, phenyl, alkoxy, preferably $C_1$–$C_6$ alkoxy, and alkylthio, preferably $C_1$–$C_6$ alkylthio. radicals and m is 1 or 2.

According to a preferred embodiment of the invention, R in formula II is hydrogen and the benzene derivative is accordingly a halobenzene, a perhaloalkoxybenzene or a perhaloalkylthiobenzene.

More preferentially still, the benzene derivative is chosen from among the halobenzenes and is, very especially, fluorobenzene.

The invention is particularly suitable for employing $COCl_2$, because the latter is the industrially most easily obtainable compound of the formula I.

The hydrofluoric acid employed is preferably anhydrous.

The use of aqueous hydrofluoric acid would entail a useless consumption of boron trifluoride in the form of $HF.BF_3.H_2O(H_3O^+BF_4^-)$.

It is preferable to employ an amount of $BF_3$ such that the absolute pressure of $BF_3$ in the reaction space is between 6 and 20 bars.

The higher the pressure, the higher the reaction rate. A pressure greater than 20 bars is not outside the scope of the invention but does not provide any particular advantage. A skilled worker will accordingly choose the pressure with a view to the economics of the process.

Advantageously, the molar ratio of hydrofluoric acid to benzene derivative is between 5 and 50, more especially between 10 and 30.

The molar ratio of benzene derivative to compound of the formula I is preferably between 1 and 3 and more especially about 2.

The temperature is preferably between 20° and 150° C.

The benzophenones obtained correspond to the general formula:

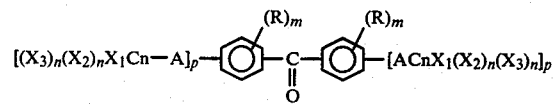

in which A, R, n, m and p have the above meanings and if n=0, $X_1$ has the above meaning, if n=1, $X_1$, $X_2$ and $X_3$ are all F because each has undergone exchange with the fluoride ions of the reaction medium and if n=2. the benzophenones obtained correspond to the following formula

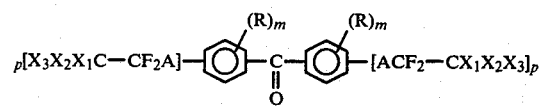

in which $X_1$, $X_2$ and $X_3$ are all defined as above, the exchange between the halogens and the fluoride ions of the reaction medium only taking place in the case of the halogens attached to the carbon in the α-position to the hetero-atom (A).

Amongst the starting benzene derivatives there may be mentioned fluorobenzene, chlorobenzene, bromobenzene, iodobenzene, the difluorobenzenes, the dichlorobenzenes, the dibromobenzenes, the chlorofluorobenzenes, the chlorobromobenzenes, the bromofluorobenzenes, trifluoromethoxybenzene, trichloromethoxybenzene, tribromomethoxybenzene, bromodichloromethoxybenzene, bromodifluoromethoxybenzene, the chlorotrifluoromethoxybenzenes, the fluorotrifluoromethoxybenzenes, trifluoromethylthiobenzene, trichloromethylthiobenzene, the chlorotrifluoromethylthiobenzenes, the fluorotrifluoromethylthiobenzenes, pentafluoroethoxybenzene, pentachloroethoxybenzene, the fluorotoluenes, the chlorotoluenes, the fluoroanisoles, the chloroanisoles, the fluorothioanisoles, the chlorophenols, the fluorophenols, the trifluoromethoxyphenols and the trifluoromethylthiophenols.

Among the benzophenones obtained by the process according to the invention there may be mentioned:

4,4'-Difluorobenzophenone, 4,4'-dichlorobenzophenone, 4,4'-dibromobenzophenone, 4,4'-bis-trifluoromethoxybenzophenone, 4,4'-bis-trifluoromethylthiobenzophenone, 4,4'-bis-α,α-difluoro-β,β,β-trichloroethoxy)-benzophenone, the difluorodimethylbenzophenones, the difluorodihydroxybenzophenones, the difluorodimethoxybenzophenones, the tetrafluorobenzophenones and the tetrachlorobenzophenones.

The benzophenones obtained by the process described above are used as synthesis intermediates in the pharmaceutical, plant protection and polymer industries (German Patent No. 2,659,580 and U.S. Pat. No. 3,732,307).

The invention will now be described more completely with the aid of the examples which follow.

EXAMPLE 1

Into a stainless steel reactor which is stirred magnetically and cooled to about 0° C. by means of an iced water bath there are introduced 100 g (5 moles) of anhydrous hydrofluoric acid, 9.6 g (0.1 mole) of fluorobenzene and 5 g (0.05 mole) of phosgene.

The reactor is closed and boron trifluoride to a pressure of 6 bars is then introduced. Thereafter the reaction mixture is heated to 80° C., with stirring, for 3 hours. After it has been cooled to ambient temperature and the pressure released, the crude reaction mixture is poured onto 200 g of ice and the heterogeneous mixture thus obtained is extracted with 3 times 100 ml of methylene chloride. The organic phase is washed twice with 150 ml of water and then dried. After evaporation, 7.2 g (yield: 66%) of a mixture containing 75% of 4,4'-difluorobenzophenone and 25% of 2,4'-difluorobenzophenone (liquid phase chromatography analyses) is obtained.

EXAMPLE 2

A procedure analogous to Example 1 is employed, with the following compounds and the same general conditions:

| | |
|---|---|
| hydrofluoric acid | 100 g (5 moles) |
| trifluoromethoxybenzene | 32.4 g (0.2 mole) |
| phosgene | 9.9 g (0.1 mole) |
| $BF_3$ | 6 bars at 20° C. |
| temperature | 80° C. |
| duration | 3 hours 40 minutes |

14.4 g (yield: 41.1%) of a mixture essentially consisting of 4,4'-bis-trifluoromethoxybenzophenone and 2,4'-bis-trifluoromethoxybenzophenone (analyses by gas phase chromatography, infrared and mass spectrometry) is obtained.

EXAMPLE 3

A procedure analogous to Example 1 is employed, with the following compounds and conditions:

| | |
|---|---|
| hydrofluoric acid | 50 g (2.5 moles) |
| chlorobenzene | 11.2 g (0.1 mole) |
| phosgene | 6.5 g (0.065 mole) |
| $BF_3$ | 10 bars (at 20° C.) |
| temperature | 120° C. |
| duration | 23 hours 15 minutes |

7 g (yield = 55%) of a mixture essentially consisting of 4,4'-dichlorobenzophenone and 2,4'-dichlorobenzophenone (analyses by gas phase chromatography and infrared) is obtained.

EXAMPLE 4

A procedure analogous to Example 1 is employed, with the following compounds and conditions:

| | |
|---|---|
| hydrofluoric acid | 50 g (2.5 moles) |
| m-dichlorobenzene | 14.7 g (0.1 mole) |
| phosgene | 6.5 g (0.065 mole) |
| $BF_3$ | 10 bars at 20° C. |
| temperature | 120° C. |
| duration | 23 hours |

Infrared and gas phase chromatography analyses on the crude product show the presence of about 7% of a mixture of tetrachlorobenzophenones.

We claim:

1. A process for the preparation of benzophenones comprising the step of reacting a compound of the formula $COX_4X_5$ (I), where $X_4$ and $X_5$ are identical or different and each is a halogen atom, with a deactivated benzene derivative in liquid hydrofluoric acid and in the presence of boron trifluoride ($BF_3$) in an amount sufficient that the absolute pressure of ($BF_3$) is at least 1 bar.

2. The process of claim 1, wherein said deactivated benzene derivative has the formula:

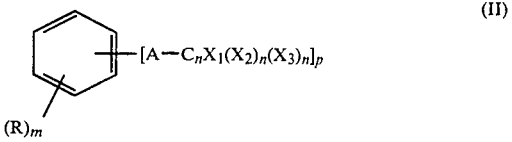

(II)

where
A is a covalent bond, an oxygen atom, or a sulfur atom,
$X_1$, $X_2$ and $X_3$ are identical or different and each is a halogen atom,
n is between 0 and 2 and if A is a covalent bond, n is 0,
R is a moiety selected from the group consisting of hydrogen, halogen, hydroxyl, alkyl, phenyl, alkoxy and alkylthio,
m is 1 or 2, and
p is 1 or 2.

3. The process of claim 2, wherein R in formula (II) is hydrogen.

4. The process of claim 3, wherein n in formula (II) is 0.

5. The process of claim 2, wherein n in formula (II) is 0.

6. The process of claim 2, wherein the benzene derivative is fluorobenzene.

7. The process of claim 6, wherein n in formula (II) is 0.

8. The process of claim 1, wherein $X_4$ and $X_5$ in formula (I) are both Cl.

9. The process of claim 1, wherein the hydrofluoric acid is anhydrous.

10. The process of claim 1, wherein the $BF_3$ is present in an amount sufficient that the absolute pressure of $BF_3$ ranges from about 6 to 20 bars.

11. The process of claim 1 wherein the molar ratio of hydrofluoric acid to deactivated benzene derivative ranges from about 5 to 50.

12. The process of claim 1, wherein the molar ratio of deactivated benzene derivative to compound of the formula I ranges from about 1 to 3.

13. The process of claim 1, wherein the reaction is carried out at a temperature ranging from about 20° to 150° C.

14. The process of claim 13, wherein the hydrofluoric acid is anhydrous, wherein the $BF_3$ is present in an amount sufficient that the absolute pressure of $BF_3$ ranges from about 6 to 20 bars, where the molar ratio of hydrofluoric acid to deactivated benzene derivative ranges from about 5 to 50, and wherein the molar ratio of deactivated benzene derivative to compound of the formula I ranges from about 1 to 3.

15. The process of claim 1, wherein said compound of the formula $COX_4X_5$ is phosgene, wherein said deactivated benzene derivative is selected from the group consisting of fluorobenzene, trifluoromethoxybenzene, chlorobenzene and m-dichlorobenzene, wherein said hydrofluoric acid is anhydrous, wherein the absolute pressure of $BF_3$ is from 6 to 10 bars, wherein the temperature of the reaction is from 80° to 120° C., wherein the molar ratio of hydrofluoric acid to deactivated benzene derivative is from 25 to 50, and wherein the molar ratio of deactivated benzene compound to compound of the formula I is from about 1.5 to 2.

* * * * *